(12) United States Patent
De Morree et al.

(10) Patent No.: US 10,966,616 B2
(45) Date of Patent: Apr. 6, 2021

(54) ASSESSING SYSTEM AND METHOD FOR CHARACTERIZING RESTING HEART RATE OF A SUBJECT

(71) Applicant: KONINKLIJKE PHILIPS N.V., Eindhoven (NL)

(72) Inventors: Helma Majella De Morree, Waalre (NL); Alberto Giovanni Bonomi, Eindhoven (NL); Francesco Sartor, Eindhoven (NL); Alphonsus Tarcisius Jozef Maria Schipper, Stramproy (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 67 days.

(21) Appl. No.: 16/096,987

(22) PCT Filed: May 2, 2017

(86) PCT No.: PCT/EP2017/060326
§ 371 (c)(1),
(2) Date: Oct. 26, 2018

(87) PCT Pub. No.: WO2017/191085
PCT Pub. Date: Nov. 9, 2017

(65) Prior Publication Data
US 2019/0142282 A1    May 16, 2019

(30) Foreign Application Priority Data
May 4, 2016    (EP) ..................................... 16168240

(51) Int. Cl.
*A61B 5/0205* (2006.01)
*A61B 5/00* (2006.01)
(Continued)

(52) U.S. Cl.
CPC ........ *A61B 5/0205* (2013.01); *A61B 5/02405* (2013.01); *A61B 5/11* (2013.01);
(Continued)

(58) Field of Classification Search
CPC .............................. A61B 5/0205; G15H 40/63
(Continued)

(56) References Cited

U.S. PATENT DOCUMENTS

2008/0281370 A1    11/2008    Lin et al.
2014/0206977 A1    7/2014    Bahney et al.
(Continued)

FOREIGN PATENT DOCUMENTS

WO    2014152212 A1    9/2014
WO    2015036289 A1    3/2015
(Continued)

OTHER PUBLICATIONS

International Search Report and Written Opinion for International Application No. PCT/EP2017/060326 filed May 2, 2017, 19 pages.

*Primary Examiner* — Nadia A Mahmood (57) ABSTRACT

The present invention relates to an assessing system, an assessing method and a computer program for assessing a heart rate of a subject. It finds application in categorizing a physiological response as a condition, in particular in the diagnosis of pathological tachycardia and bradycardia. The assessing system comprises a photoplethysmography (PPG) signal providing unit (10); a motion signal providing unit (20); a parameter providing unit (30) for providing a subject specific parameter; a heart rate determination unit (40); a resting period determination unit (50); an abnormality determination unit (80) for determining an abnormality of the heart rate during the resting period; and an assessing unit (90) for assessing the determined abnormality based on the subject specific parameter. The invention provides a system
(Continued)

and a method, which allow for a more reliable assessment of a heart rate of a subject based on a PPG signal of the subject.

17 Claims, 5 Drawing Sheets

(51) Int. Cl.
*A61B 5/024* (2006.01)
*A61B 5/11* (2006.01)
*G16H 40/63* (2018.01)
*G16H 50/20* (2018.01)
*A61B 5/16* (2006.01)

(52) U.S. Cl.
CPC ............ *A61B 5/681* (2013.01); *A61B 5/7221* (2013.01); *G16H 40/63* (2018.01); *A61B 5/02416* (2013.01); *A61B 5/02438* (2013.01); *A61B 5/1118* (2013.01); *A61B 5/165* (2013.01); *A61B 5/4806* (2013.01); *A61B 5/6824* (2013.01); *A61B 5/7207* (2013.01); *A61B 2562/0219* (2013.01); *G16H 50/20* (2018.01)

(58) Field of Classification Search
USPC ........................................................ 600/301
See application file for complete search history.

(56) References Cited

U.S. PATENT DOCUMENTS

2015/0282717 A1* 10/2015 McCombie ........... A61B 5/1116
600/301
2016/0051154 A1* 2/2016 Iwawaki .............. A61B 5/0245
600/483

FOREIGN PATENT DOCUMENTS

| WO | 2015066430 | A1 | 5/2015 |
| WO | 2015107891 | A1 | 7/2015 |
| WO | 2015189304 | A1 | 12/2015 |

* cited by examiner

ASSESSING SYSTEM AND METHOD FOR CHARACTERIZING RESTING HEART RATE OF A SUBJECT

This application is the U.S. National Phase application under 35 U.S.C. § 371 of International Application No. PCT/EP2017/060326, filed on May 2, 2017, which claims the benefit of European Application Serial No. 16168240.6 filed May 4, 2016. These applications are hereby incorporated by reference herein.

FIELD OF THE INVENTION

The present invention relates to an assessment of a heart rate of a subject. In particular, it relates to an assessing system, an assessing method and a computer program for assessing a heart rate of a subject. It finds application in categorizing a physiological response as a condition, in particular in the diagnosis of pathological tachycardia and bradycardia. However, it is to be understood that the present invention also finds application in other fields and is not necessarily limited to the above-mentioned application.

BACKGROUND OF THE INVENTION

A healthy adult heart normally beats within a certain frequency range during rest. Tachycardia, i.e. the heart rate being too fast, or bradycardia, i.e. the heart rate being too slow, can be indicative of heart problems.

Assessing conditions of a heart rate from an electrocardiogram (ECG) recording can be done based on the heart rate and rhythm and additionally on the ECG morphology. Employing photoplethysmography (PPG) signals is desired, since PPG sensors can be integrated in a less obtrusive device and thus conveniently provide a signal over a long time. However, in the PPG wave form, no specific information on the electro-mechanical activity of the heart is present, contrarily to what is provided by an ECG signal so that other means of differentiating normal from abnormal rhythms are needed.

WO 2015/107891 A1 discloses a biological information processing system including a heart rate information acquisition unit that acquires heart rate information of a user, a determination unit that determines a basal heart rate based on the heart rate information, and an update unit that determines an update condition of the basal heart rate and performs update processing of the basal heart rate if a determination that the update condition is satisfied is made.

US 2016/0051154 A1 discloses a biological information detecting device including a first detection unit detecting biological information of a user, an abnormality determination unit determining whether or not an abnormality occurs in the user on the basis of the biological information detected by the first detection unit, and a frequency change unit changing a detection frequency of the first detection unit to a second frequency higher than a first frequency when the occurrence of the abnormality is determined by the abnormality determination unit.

WO 2015/189304 A1 discloses a heart rate monitor system comprising an inactivity determining unit for determining periods of inactivity of a user based on motion data detected by at least one motion sensor attached to the user and a resting heart rate calculating unit for calculating a resting heart rate of the user based on heart rate data detected by at least one heart rate sensor attached to the user during the periods of inactivity as determined by the inactivity determining unit is provided.

SUMMARY OF THE INVENTION

It is thus an object of the present invention to provide a system and a method, which allow for a more reliable assessment of a heart rate of a subject based on a PPG signal of the subject.

In a first aspect of the present invention, an assessing system for assessing a heart rate of a subject is provided. The assessing system comprises: a PPG signal providing unit for providing a PPG signal indicative of a heartbeat of the subject; a motion signal providing unit for providing a motion signal indicative of a motion of the subject; a parameter providing unit for providing a subject specific parameter of the subject; a heart rate determination unit for determining a heart rate of the subject based on the PPG signal; a resting period determination unit for determining a resting period during which the subject is at rest based on the motion signal; an abnormality determination unit for determining an abnormality of the heart rate during the resting period, wherein the abnormality determination unit is arranged to determine bradycardia and/or tachycardia based on an upper and lower threshold of the heart rate, respectively, as the abnormality of the heart rate; and an assessing unit for assessing a pathological origin of the determined abnormality based on the subject specific parameter.

Since the resting period determination unit determines the resting period as a period during which the subject is at rest, the resting period indicates the time during which the PPG signal is not under the influence of strong motion or activity of the subject and thus a reliability of the PPG signal is increased when only considering the resting period.

Since the abnormality determination unit determines an abnormality based on the resting period, more precisely based on the heart rate during the resting period, motion influence of the subject, such as when the subject is active, will advantageously not lead to a compromised determination result. Further, since the assessing unit assesses the determined abnormality based on the subject specific parameter, also the assessing will not be compromised by a compromised abnormality. Even further, since the assessing by the assessing unit is performed based on the subject specific parameter, the assessing can be performed more accurately and reliably.

The PPG signal providing unit can be a storing unit, in which the PPG signal is stored already, wherein the PPG signal providing unit can be adapted to provide the stored PPG signal. However, the PPG signal providing unit can also be a receiving unit for receiving a PPG signal from a PPG signal measurement unit such as a PPG sensor and for providing the received PPG signal. Moreover, the PPG signal providing unit can be the PPG signal measurement unit itself, wherein the PPG signal providing unit provides the measured PPG signal. The PPG signal measurement unit preferentially comprises one or more light sources for illuminating a part of the subject's body and one or several detectors for detecting the light from the subject's body, wherein the PPG signal measurement unit is preferentially adapted to determine the PPG signal based on the detected light. In a preferred embodiment the PPG signal measurement unit is a pulse oximeter or a heart beat detector.

Likewise, the motion signal providing unit can be a storing unit, in which the motion signal is stored already, wherein the motion signal providing unit can be adapted to provide the stored motion signal. However, the motion signal providing unit can also be a receiving unit for receiving a motion signal from a motion signal measurement unit and for providing the received motion signal. Moreover, the motion signal providing unit can be the motion signal measurement unit itself, wherein the motion signal providing unit provides the measured motion signal.

Preferentially, the PPG signal providing unit and the motion signal providing unit provide a PPG signal and a motion signal, respectively, which originate from the same body part of the subject, such as the wrist. Preferentially, the PPG signal providing unit is the PPG signal measurement unit and the motion signal providing unit is the motion signal measurement unit and the PPG signal measurement unit and the motion signal measurement unit measure the PPG signal and the motion signal, respectively, at the same body part of the subject, such as the wrist.

Preferentially, the PPG signal and the motion signal are synchronous signals and correspond to the same time periods.

Also the parameter providing unit can be a storing unit, in which the subject specific parameter is stored already, wherein the parameter providing unit can be adapted to provide the stored subject specific parameter. However, the parameter providing unit can also be a receiving unit for receiving a subject specific parameter from an input unit, such as a user interface operable by the subject, or from another system, such as a remote server, which is arranged for transmitting the subject specific parameter to the parameter providing unit.

The heart rate determination unit can determine an instantaneous heart rate of the subject based on the PPG signal. More precisely, the heart rate determination unit can be arranged for determining features detectable in the PPG signal, such as peaks corresponding to heartbeats, and determine the heart rate based on the time difference between two consecutive peaks detectable in the PPG signal. However, the heart rate determination unit can also determine a time series of the heart rate and store the determined heart rate, such as within a storage unit provided in the assessing system.

An abnormality can be defined as any characteristic of the heart rate, which is not normal for a human being. Examples for such abnormalities include, without being limited, an unusual high heart rate (tachycardia), an unusual low heart rate (bradycardia), an irregularity in the heart rate or an unusual change of the heart rates.

The assessing unit can be arranged to assess the determined abnormality under aspects such as likelihood, reliability and origin, without being limited thereto.

The assessing unit is arranged to assess whether the abnormality is of pathological origin or not.

In an embodiment the assessing system further comprises a heart rate histogram determination unit for determining a histogram of values of the heart rate during the resting period, wherein the abnormality determination unit is arranged for determining the abnormality of the heart rate based on the histogram.

Preferentially, the heart rate histogram determination unit is arranged for receiving the heart rate from the heart rate determination unit and for counting the occurrence of a particular heart rate in a bin of the histogram. Preferentially, each bin of the histogram has a width of one beat per minute, for instance, 60 bpm or 61 bpm, et cetera. However, the resolution of the histogram is of course not limited to the width of 1 beat per minute per bin and can include other ranges in other embodiments, such as 0.5 or 3 bpm to give examples.

In this embodiment, the heart rate histogram determination unit is arranged to receive the heart rate during the resting period only. However, in other embodiments, the heart rate histogram determination unit can also receive the heart rate for all time periods and be arranged for determining the histogram based on values of the heart rate received from the heart rate determination unit which originate from the resting period only. In essence, it is important that the histogram be constituted by heart rates originating from the resting period only, such that no activity of the subject can compromise the histogram. Accordingly, since the abnormality of the heart rate is determined based on the histogram, it can be determined with an increased accuracy.

In an embodiment the assessing system further comprises a heart rate distribution determination unit for determining a distribution of the values of the heart rate based on the histogram of values of the heart rate, wherein the abnormality determination unit is configured for determining the abnormality of the heart rate based on the distribution.

In general, in addition to measurement errors and determination uncertainties, the heart rate of the subject will vary over time, even when the subject is at rest. Accordingly, also during the resting period, a distribution of the values of the heart rate will be spread over multiple values of the heart rate. Determining a distribution of the heart rates based on the histogram is advantageous over using a single value, such as the mean value of the heart rate, since abnormalities of the heart rate occur at abnormal, i.e. higher or lower than normal, values that could compensate each other and result at a normal mean value, even in case abnormalities are readily detectable. The heart rate distribution determination unit is thus arranged to determine a distribution of the values such that the spreading of the heart rate over multiple values is compensated.

In an embodiment of the assessing system, the heart rate distribution determination unit is configured for determining a number of modes in the histogram and for determining a number of distributions based on the determined number of modes.

In case the histogram is not unimodal, the distribution of the histogram cannot be approximated with a single mode distribution. In this embodiment, the heart rate distribution determination unit is thus advantageously configured to first determine the number of modes and then determine individual distributions based on the earlier determined number of modes. Thus, even in case the histogram is not uni- but bi- or multimodal, the number of unimodal distributions can be determined and the appropriate number of corresponding distributions can be determined in the second step. Advantageously, the abnormality determination unit can then determine abnormalities based on all of the provided distributions.

In an embodiment of the assessing system, the motion signal providing unit is configured to provide an accelerometer signal of the subject.

The accelerometer signal can, for instance, be a signal originating from a one- or multidimensional accelerometer, such as a 3D accelerometer. In other embodiments, the motion signal providing unit can be configured to provide a vibration, rotation or a similar signal of the subject either additionally or alternatively.

In an embodiment of the assessing system, the resting period determination unit is arranged for determining an activity of the subject based on the motion signal and for determining the resting period as a period for which no activity can be determined based on the motion signal.

An activity of the subject can be, for instance, the subject undertaking running or cycling activities or the like. Preferentially, the resting period determination unit is arranged for carrying out activity type determination algorithms on the motion signal. In case an activity of the subject is determined, it can be excluded that the subject is at rest during that period.

In an embodiment of the assessing system, the resting period determination unit is arranged for determining the resting period as a period for which a magnitude of the motion signal lies below a predefined threshold.

In case no activity can be determined, the subject can still not be at rest. For instance, the subject can carry out motion, which does not lead to a detectable activity. In case the magnitude of the motion signal, such as the signal provided by the accelerometer, exceeds a predefined threshold, it can also be excluded that the subject is at rest during this period. Thus, further to detecting activities of the subject, also periods with the subject experiencing large motion magnitude can be detected and excluded from the further processing and assessing.

In an embodiment of the assessing system, the resting period determination unit is arranged for excluding a transition period following an activity from the resting period.

The exclusion of a transition period following an activity advantageously leads to a more accurate heart rate of the subject at rest, since an activity will have an influence on the heart rate even after the activity has finished. A duration of the transition period can be pre-adjusted or determined by the resting period determination unit based on the previous activity. For instance, for longer or more intense activities, a transition period could be longer than for shorter or less intense activities. In other embodiments also a transition period following a period with large motion signal magnitude can be additionally or alternatively contemplated.

In an embodiment of the assessing system, the abnormality determination unit is arranged to determine bradycardia and/or tachycardia based on an upper and lower threshold of the heart rate, respectively, as the abnormality of the heart rate.

The abnormality determination unit is preferentially adapted to determine an abnormality by comparing the heart rate with a threshold for the heart rate and confirming an abnormality in case the heart rate exceeds or falls below the predetermined threshold. In one embodiment, the abnormality determination unit can determine the abnormality in case the heart rate exceeds an upper threshold or falls below a lower threshold once. Preferentially, the abnormality determination unit determines the abnormality in case the threshold is exceeded or fallen below for a significant amount of the recorded heart rates. For instance, based on the histogram or the distribution determined in the histogram, the abnormality determination unit can determine the ratio of the recorded heart rates being above or below the respective threshold. Thus, advantageously, statistical errors or measurement errors occurring at very high or very low heart rates are not considered for determining the abnormality.

Usually, a normal heart rate of a human subject addressed is between 60 and 100 beats per minute. A slower than normal heart rate is referred to as bradycardia and a higher than normal heart rate is referred to as tachycardia. Preferably, the upper threshold for determining tachycardia is thus 100 beats per minute and the lower threshold for determining bradycardia is defined at 60 beats per minute. The abnormality determination unit can be predefined with these thresholds or receive these thresholds from the subject, such as from the parameter providing unit. Also, in other embodiments, the thresholds can be at different values or even dynamically change.

In an embodiment of the assessing system, the abnormality determination unit will compare each of the distributions of the histogram of the heart rate with the respectively provided thresholds. In case a majority of the values of each of the distributions exceeds or falls below the respective threshold, an abnormality will be determined. In this embodiment, the majority corresponds to more than 50% of the values underlying the distribution. In one example, this can be calculated by an integral over the distribution starting from the respective threshold. However, in other embodiments, also other calculation methods can be used. Further, also other criteria than the majority of the distribution, such as 30%, 40% or also more than 50% can be used for determining the presence of an abnormality.

In an embodiment of the assessing system, the parameter providing unit is arranged to provide at least one of a profile, symptoms, a medication, a sleep profile, a fitness level and a stress level as the subject specific parameter.

A profile can be a user profile of the subject and comprise information such as the age, the height and the weight of the subject. The profile can for example be beneficial for the assessment as the heart rate of the subject at rest varies with the age of the subject. More specifically, children and adolescents or young subjects in general can have a higher resting heart rate than adults, and females can have higher resting heart rates than males. The user profile may also indicate the relative risk of that person to experience a pathological heart condition. The user profile, symptoms and medication can be entered by the user, for instance via a user interface, or transferred to the parameter providing unit of the assessing system, for instance, from a remote server via the Internet.

Further parameters, such as the sleep profile, the fitness level and the stress level can also be entered by the user, for instance via a user interface, or transferred to the parameter providing unit of the assessing system, for instance, from a remote server via the Internet. However, the sleep profile, the fitness level and the stress level can also be determined by a dedicated sleep profile determination unit, a fitness level determination unit and a stress level determination unit based on, for instance, at least one of the PPG signal, the motion signal, the activity of the user, the heart rate or another parameter. Of course, in other embodiments also additional or other subject specific parameters can be employed for the assessment carried out by the assessing unit.

In an embodiment of the assessing system, the assessing unit is configured to, in case the abnormality determination unit determines bradycardia as the abnormality, assess the determined abnormality based on the profile, the symptoms, the medication, the sleep profile and the fitness level of the subject. Preferably, the assessing unit can be arranged to assess whether or not the determined bradycardia is of pathological origin. For instance, in case the symptoms indicate one of fatigue, dizziness, light-headedness, fainting or near-fainting spells, and in extreme cases, cardiac arrest, a pathological origin of bradycardia is more likely since it can cause insufficient blood flow to the brain which could lead to these symptoms. As to medication, digoxin and certain antiarrhythmic agents, especially beta-blockers or amiodarone, can lead to sinus and thus non-pathological bradycardia. Also certain eye drops (for instance, timolol) might cause sinus bradycardia. Non-pathological bradycardia is more likely and more usual to occur during sleep and non-pathological bradycardia is common in healthy, athletic individuals. In other embodiments, also additional or alternative parameters can be considered for assessing bradycardia.

In an embodiment of the assessing system, the assessing unit is configured to, in case the abnormality determination unit determines tachycardia as the abnormality, assess the determined abnormality based on the profile, the symptoms, the medication, the sleep profile and the stress level of the subject. Preferably, the assessing unit can be arranged to assess whether or not the determined tachycardia is of pathological origin. For example, pathological tachycardia can cause symptoms such as dizziness, light-headedness, rapid heartbeat or palpitations, angina (chest pain), shortness of breath, unconsciousness, or cardiac arrest. Sinus tachycardia may present during conditions such as fever, pain, or dehydration. As to medication, bronchodilators or dopamine could lead to sinus tachycardia, as well as omitting beta-blocker medication. Also the use of caffeine and alcohol can induce tachycardia. Non-pathological tachycardia is less likely to occur during sleep and non-pathological tachycardia may occur as a consequence of mental stress. In other embodiments, also additional or alternative parameters can be considered for assessing tachycardia.

In an embodiment the assessing system is implemented as a wrist based device. In this embodiment, the assessing system is preferably provided in the form of a watch-like device, a bracelet-like device or the like. In other embodiments, one or more units of the assessing system can also be provided distant or remote from the wrist-based or wrist-worn device. The wrist-worn device can then further comprise a communication unit for communicating, such as for data transmission via the Internet, with a remote unit, for instance a server.

In an embodiment the assessing system further comprises a feedback providing unit for providing feedback to the subject.

In this embodiment, the subject may be a user using the assessing system. The feedback providing unit can be arranged for informing the subject of abnormalities determined from the heart rate. Further, the feedback providing unit can provide information on a result of the assessing by the assessing unit. For instance, in one embodiment, the subject can be informed that bradycardia and/or tachycardia episodes that have occurred during the period the assessing system has assessed, the subject is informed whether the origin is likely pathological or non-pathological. For instance, the subject can be informed that most likely the abnormal episode is of physiological origin or that strong indications are present that the anomaly is of pathological origin. In this case, the subject can be advised to consult the health care professional, for instance. The feedback providing unit can in one embodiment be a display unit integrated within the wrist-based device. In another embodiment, the feedback providing unit can also be a transmission unit for transmitting the feedback indirectly to the subject, for instance via a known wireless or wire-based transfer protocol, via a server or a handheld device of the subject, such as a Smartphone. The subject can then access the provided feedback by using his/her computer, tablet, Smartphone or the like.

The heart rate determination unit, the heart rate histogram determination unit, the heart rate distribution determination unit, the resting period determination unit, the abnormality determination unit and the assessing unit can in one embodiment be provided in one or more processors that are arranged in the same or different physical devices. More precisely, the heart rate determination unit, the heart rate histogram determination unit, the heart rate distribution determination unit, the resting period determination unit, the abnormality determination unit and the assessing unit can in one embodiment be provided together with the PPG signal providing unit and/or the motion signal providing unit and/or the parameter providing unit in a single device or in a different embodiment be distributed over multiple devices.

In one embodiment the heart rate determination unit, the heart rate histogram determination unit, the heart rate distribution determination unit, the resting period determination unit, the abnormality determination unit and the assessing unit are adapted for communicating with the PPG signal providing unit and/or the motion signal providing unit and/or the parameter providing unit in a wired or wireless manner as well known in the art. In one embodiment, one, more or all of the heart rate determination unit, the heart rate histogram determination unit, the heart rate distribution determination unit, the resting period determination unit, the abnormality determination unit and the assessing unit are provided at a server, which is arranged for communicating with the rest of the assessing system by suitable communication means, for instance via the Internet.

In a further aspect of the invention an assessing method for assessing a heart rate of a subject is provided. The assessing method comprises: providing a photoplethysmography signal indicative of a heartbeat of the subject; providing a motion signal indicative of a motion of the subject; providing a subject specific parameter of the subject; determining a heart rate of the subject based on the photoplethysmography signal; determining a resting period during which the subject is at rest based on the motion signal; determining an abnormality of the heart rate based on the resting period; and assessing the determined abnormality based on the subject specific parameter.

In a further aspect of the invention a computer program for assessing a heart rate of a subject is provided, the computer program comprising program code means for causing an assessing system as defined in claim 1 to carry out the assessing method as defined in claim 14, when the computer program is run on the assessing system.

It shall be understood that the assessing system for assessing a heart rate of a subject of claim 1, the assessing method for assessing a heart rate of a subject of claim 14 and the computer program for assessing a heart rate of a subject of claim 15 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
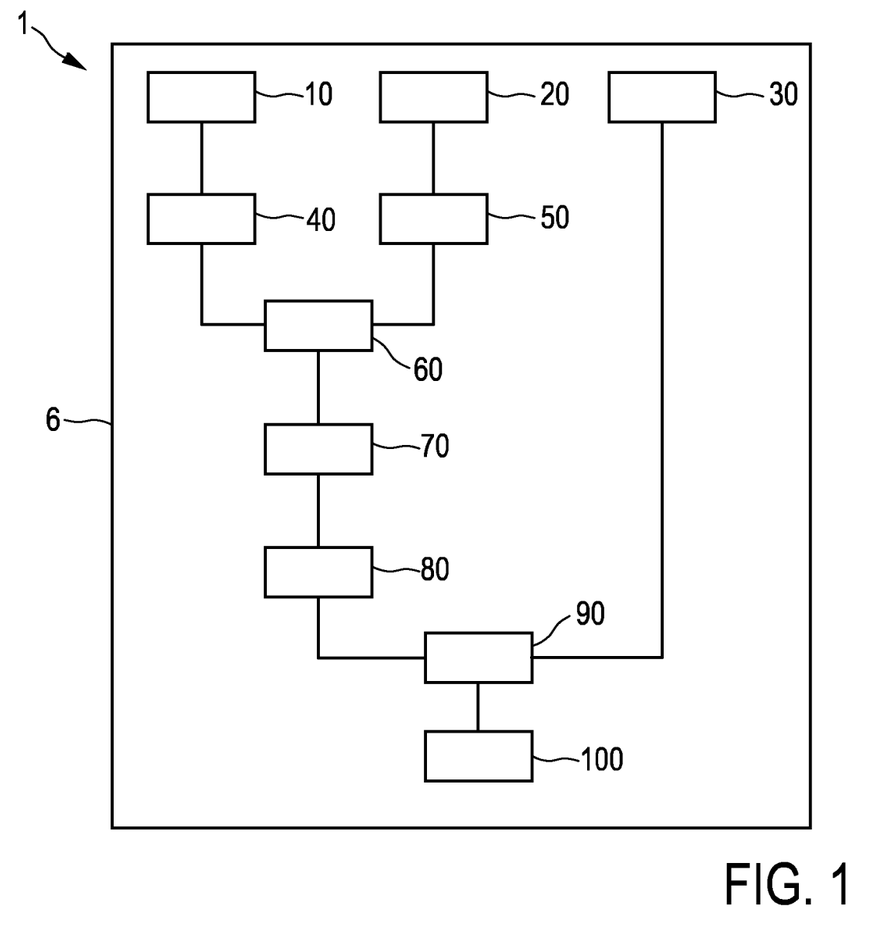
FIG. 1 schematically and exemplarily shows an embodiment of an assessing system for assessing a heart rate of a subject, FIG. 2 schematically and exemplarily shows a watch-like device as an embodiment of the assessing system shown in FIG. 1, FIG. 3 schematically and exemplarily illustrates a histogram of resting heart rates of the subject, FIG. 4 schematically and exemplarily illustrates an example of separating a bimodal histogram into distributions, FIG. 5 schematically and exemplarily illustrates a histogram with a threshold, and FIG. 6A-6C schematically and exemplarily illustrate a flowchart of an example of an assessing method according to the invention.

FIG. 1 schematically and exemplarily shows an embodiment of an assessing system 1 for assessing a heart rate of a subject. Assessing system 1 comprises a PPG signal providing unit 10, a motion signal providing unit 20, a parameter providing unit 30, a heart rate determination unit 40, a resting period determination unit 50, a heart rate histogram determination unit 60, a heart rate distribution determination unit 70, an abnormality determination unit 80, an assessing unit 90 and a feedback providing unit 100. In this example, all units of assessing system 1 are contained within a casing 6. However, in other examples, also one or several of the units of assessing system 1 can be provided remote from casing 6, such as at a central server, and communicate with assessing system 1 by any known wired or wireless means. Further, in other examples, assessing system 1 is fully implemented as units within a computer system and must not comprise casing 6.

PPG signal providing unit 10 in this example is a PPG signal measurement unit comprising a PPG sensor for measuring a PPG. This unit can be a known PPG sensor unit, which comprises light-emitting diodes (LEDs) directing light onto the skin of the subject and which detects light reflected from the skin of the subject, wherein PPG sensor unit 10 generates the PPG based on the detected light.

Motion signal providing unit 20 in this example comprises an accelerometer, which detects accelerations of body parts of the subject. In this example, the accelerometer comprises a multi-dimensional accelerometer in order to detect posture changes of the subject by observing changes in average orientation of the accelerometer with respect to gravity. However, in other embodiments, other means and units for providing the motion signal are contemplated.

Parameter providing unit 30 is in this example a parameter input unit into which a user can input at least one subject-specific parameter. Parameter providing unit 30 comprises a user operable touchscreen (not shown) or any other suitable input device such that the subject can perform the desired input operations. The subject-specific parameter can be, for instance, one of a profile, symptoms and/or medication of the subject. The user or subject profile can comprise the age, height and weight information of the subject. To facilitate the input, the subject can in this example select symptoms and medication from a predefined list. In other examples, parameter providing unit 30 can also provide subject-specific parameters transferred from a remote system, such as from a user profile via the Internet. Further, it is well-known that other means for inputting subject-specific data can also be implemented.

Parameter providing unit 30 is further arranged for providing subject-specific parameters, which are not to be inputted by the subject. For instance, parameter providing unit 30 can provide a sleep profile, a fitness level and/or a stress level of the subject based on calculations done within assessing system 1 based on, for instance, the PPG signal and/or the motion signal.

Heart rate determination unit 40 determines the heart rate of the subject based on the PPG signal provided by PPG signal providing unit 10. Heart rate determination unit 40 determines the heart rate, for instance, by analyzing interbeat intervals between features, such as peaks, detectable in the PPG signal. Various solutions for determining a heart rate based on a PPG signal are known in the art.

Resting period determination unit 50 is arranged for determining a resting period during which the subject is at rest based on the motion signal provided by motion signal providing unit 20. Resting period determination unit 50 can, for instance, implement activity recognition algorithms that are adapted to recognize whether activities such as running or cycling are being undertaken by the subject. If activities can be excluded, a further distinction as to whether the subject is at rest can be made based on the level of activity determined from a magnitude of the motion signal. In case no activity can be recognized and the activity level determined by the magnitude of the motion signal is below a predefined threshold, the subject is determined to be at rest. However, resting period determination unit 50 can be further adapted to consider periods following an activity period as transition periods, i.e. a period during which no activity is detectable, but the subject is nevertheless recovering from the earlier activity. The resting period will thus be the period during which the subject is at rest and not recovering from prior activity.

Heart rate histogram determination unit 60 is arranged to determine a histogram of the heart rate of the subject based on the heart rate provided by heart rate determination unit 40 and the resting period during which the subject is at rest provided by resting period determination unit 50. Heart rate histogram determination unit 60 can classify a heart rate connected with each heartbeat of the subject into one of a plurality of histogram bins. A histogram bin can, for instance, correspond to an integer value of the heart rate. For instance, the histogram bin corresponding to 60 beats per minute (bpm) can include all heartbeats corresponding to a heart rate from 59.50 to 60.49 bpm. However, also other widths of bins of the histogram are contemplated, such as a narrower or broader width. It is obvious that more histogram bins will lead to a higher resolution of the resulting distribution but will need more heartbeats and corresponding heart rates in order to have statistic significance. In this example, heart rate histogram determination unit 60 determines the histogram of the heart rate for the past 24 hours, respectively the resting periods thereof. This time frame is of course arbitrary and can be adapted as needed by the skilled person.

Heart rate distribution determination unit 70 determines a distribution of the histogram provided by heart rate histogram determination unit 60 to further analyze the distribution of the resting heart rate. In a first step, heart rate distribution determination unit 70 in this example determines whether the histogram is unimodal or bi- or multimodal. If the histogram is unimodal, only one distribution needs to be further analyzed. If the histogram is bimodal or multimodal, it needs to be determined which unimodal distributions make up the histogram. Particularly in case of a bi- or multimodal distribution, taking the mean heart rate of the histogram would not be meaningful, since it would not take into account the lowest and highest values of the heart rate, which are of particular interest. Heart rate distribution determination unit 70 determines the distributions such that the histogram provided by heart rate histogram determination unit 60 is approximated as good as possible. For instance, a correlation between the distributions and the histogram can be calculated and optimized.

Abnormality determination unit 80 determines abnormalities of the heart rate based on the at least one distribution provided by heart rate distribution determination unit 70. In this example, abnormality determination unit 80 will determine for each of the unimodal distributions provided by heart rate distribution determination unit 70 whether the majority of the heart rate values, i.e. the area under the corresponding distribution if regarded graphically, lies below or above a threshold. In case the majority of the heart rate values lie below a lower threshold, it will be determined that bradycardia is present as an abnormality of the heart rate. In case the majority of the heart rate values lie above an upper threshold, it will be determined that tachycardia is present as an abnormality in the heart rate. In case an abnormality has been determined by abnormality determination unit 80, this abnormality will be further assessed.

Assessing unit 90 assesses an abnormality determined by abnormality determination unit 80 based on subject-specific parameters provided by parameter providing unit 30. A specific exemplary implementation of assessing unit 90 will be described in further detail in the context of FIG. 6A-C below.

Feedback providing unit 100 receives the assessing result from assessing unit 90 and is arranged to provide feedback about the result of the assessment to the subject. In this example, feedback providing unit 100 can provide feedback to the subject using the same touchscreen (not shown) used for inputting information into parameter providing unit 30. However, in other examples, feedback providing unit 100 can also be adapted to transmit feedback of the user to a remote entity, such as to a server via the Internet. Also other variations are well-known to the person skilled in the art.

Figure 2:
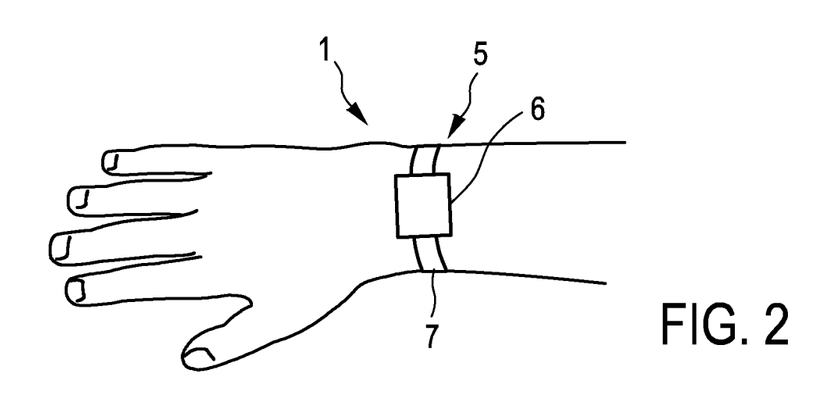

FIG. 2 exemplarily shows an example of assessing system 1 in which casing 6 is attached by means of a wrist belt 7 to a wrist 5 of the subject. Wrist 5 of the subject is a preferred location for positioning assessing system 1, since subjects are used to carrying wrist worn devices and since it is a very little obtrusive position for such devices. In other words, assessing system 1 can be worn on wrist 5 all day long, without causing substantial discomfort or the like to the subject. Nevertheless, it is well known to a person skilled in the art that assessing system 1 or casing 6, respectively, can also be attached to other parts of the subject.

Figure 3:
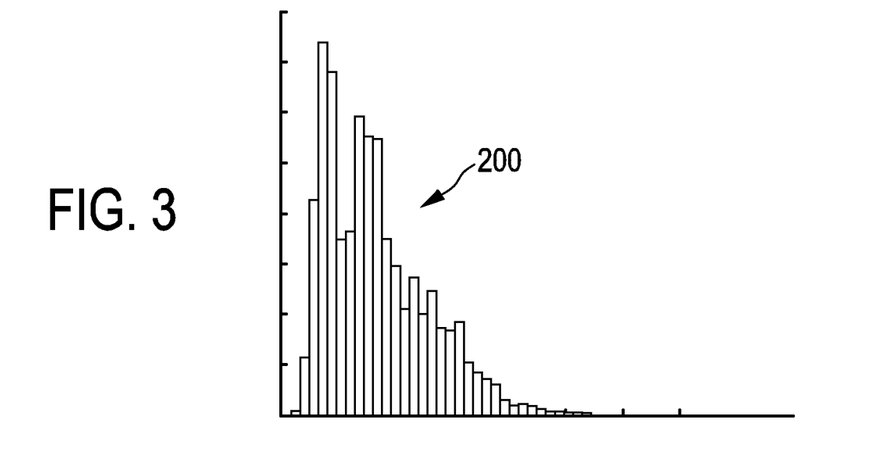

FIG. 3 schematically and exemplarily illustrates a histogram 200 determined by heart rate histogram determination unit 60 of resting heart rates of the subject. Bins of the histogram corresponding to the heart rate are provided on the horizontal axis, wherein the number of occurrences of a particular heart rate is provided on the vertical axis. In this example, histogram 200 indicates a higher probability for lower heart rates than for higher heart rates, as visible from the higher bars to the left side of histogram 200.

Figure 4:
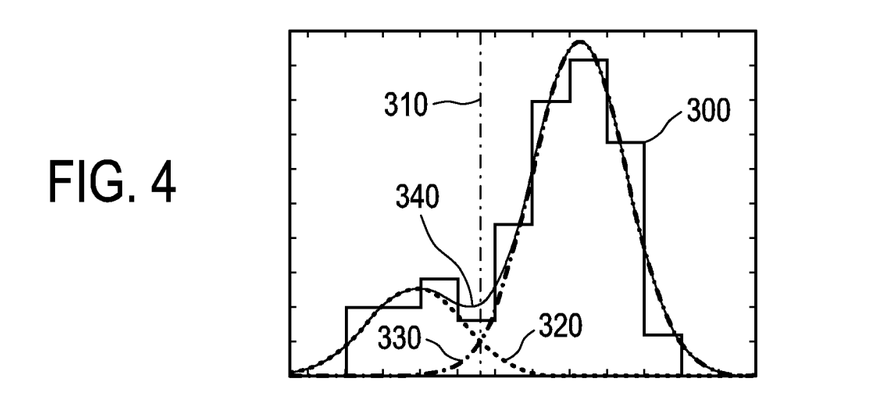

FIG. 4 shows an example of a histogram 300, which is a bimodal histogram in this example. Histogram 300 is divided by a separation 310 at a lowest value between two peak values of histogram 300. Each of the sides of separation 310 is approximated by a unimodal distribution 320 and 330, respectively. Summed up, distribution 320 and 330 approximate the complete histogram 300, indicated as complete distribution 340.

Figure 5:
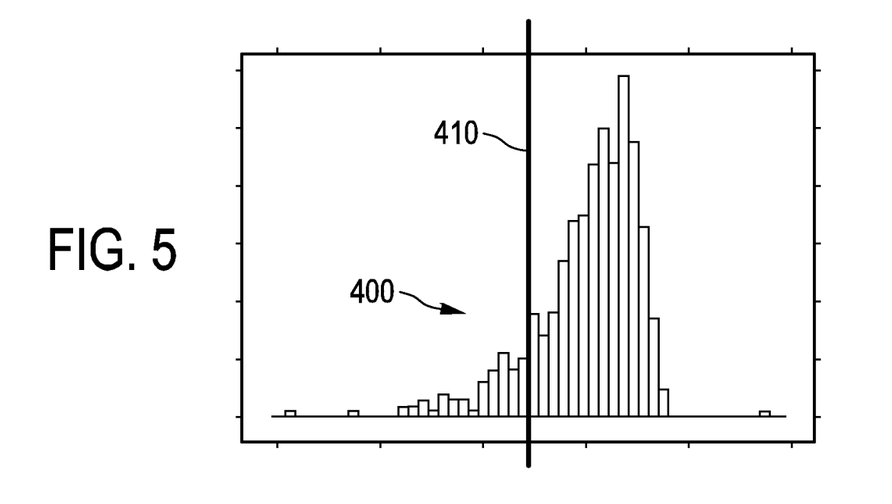

FIG. 5 is an example of a further histogram 400 in which an abnormality is detectable. It can be seen that most of the detected heart rates are above a threshold 410, which is in this example a threshold for an abnormal high heart rate, i.e. tachycardia. The majority of the heart rates is in this example to the right of threshold 410, i.e. shows a higher heart rate than the tachycardia threshold.

Figure 6A:
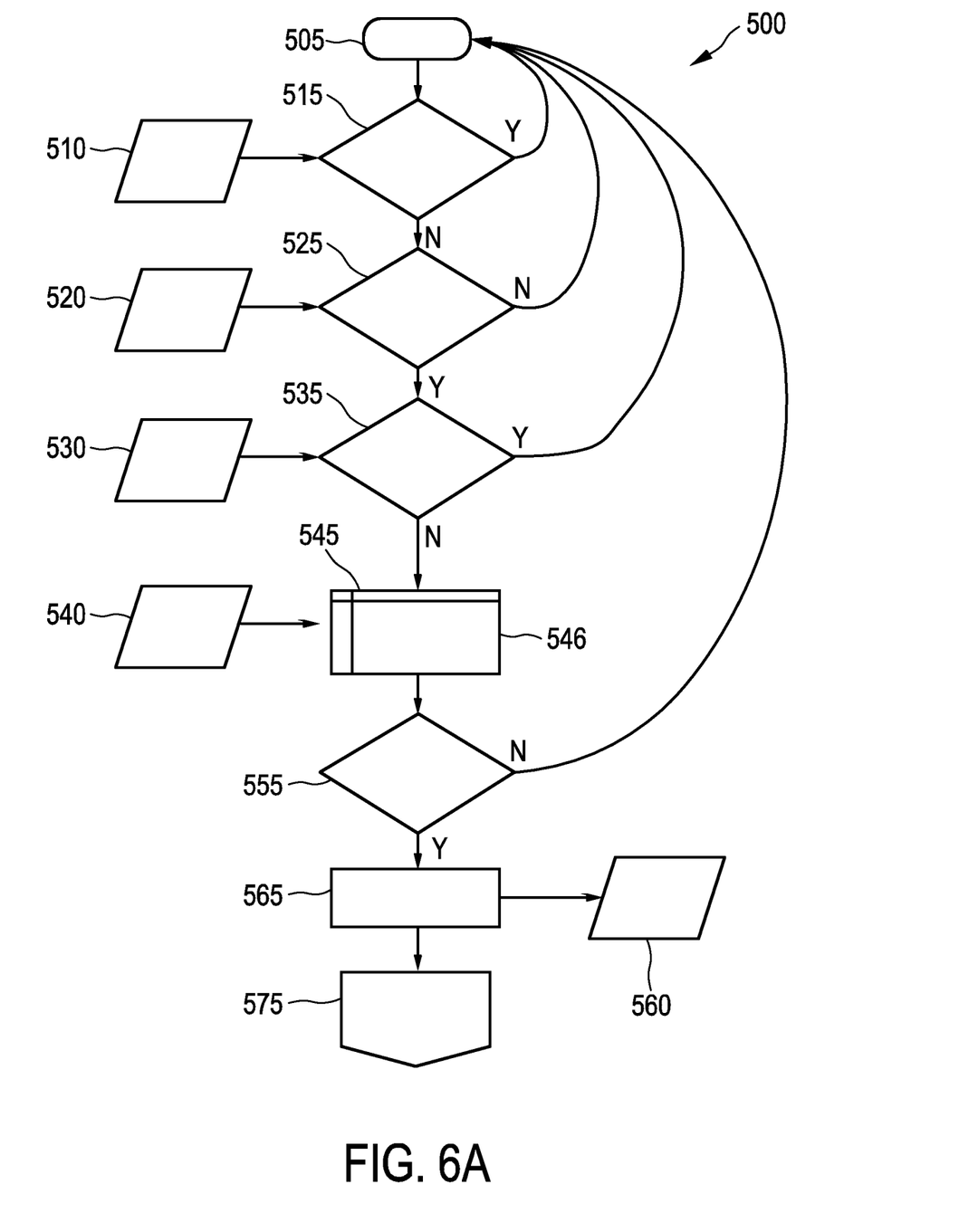
Figure 6B:
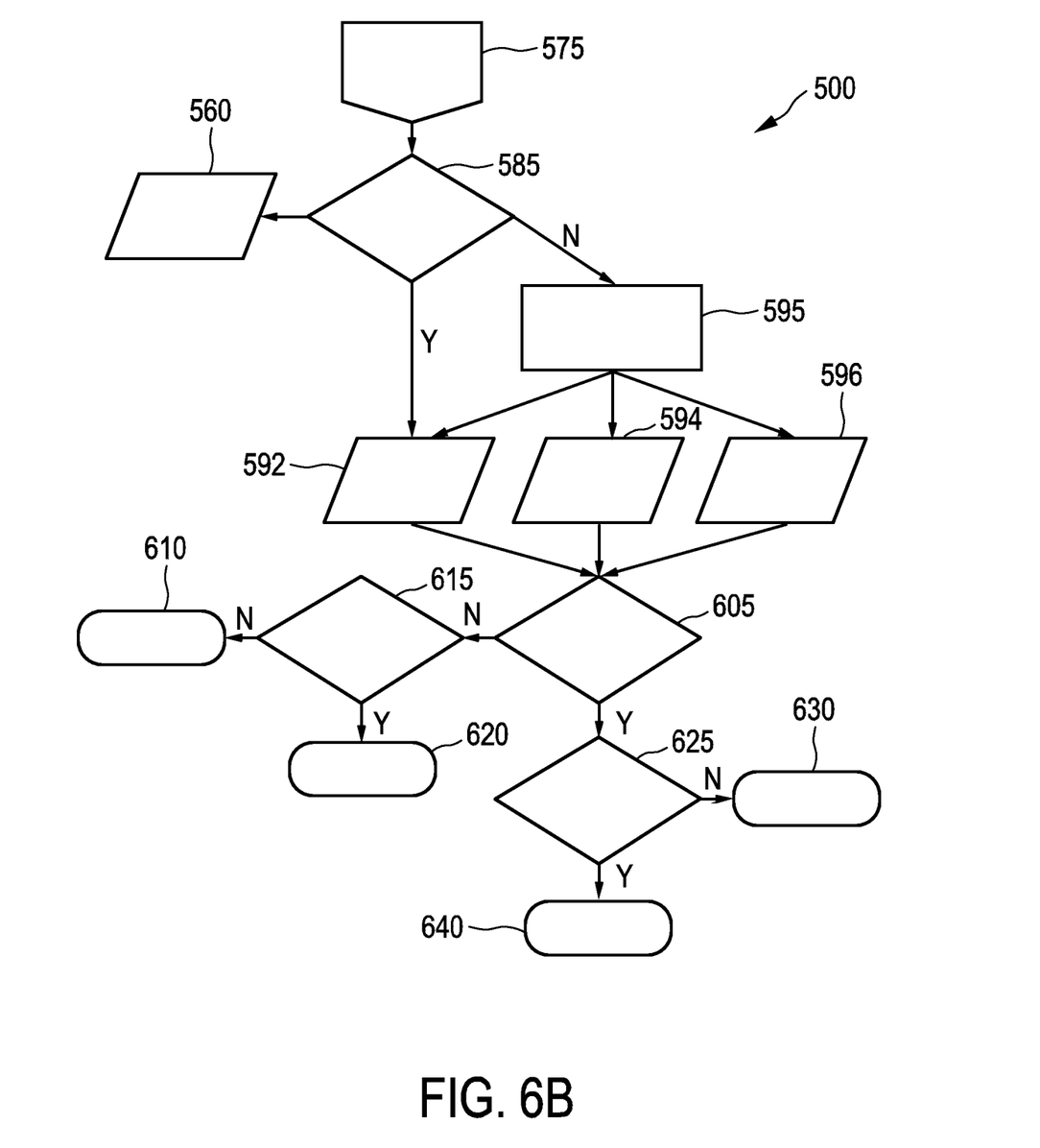
Figure 6C:
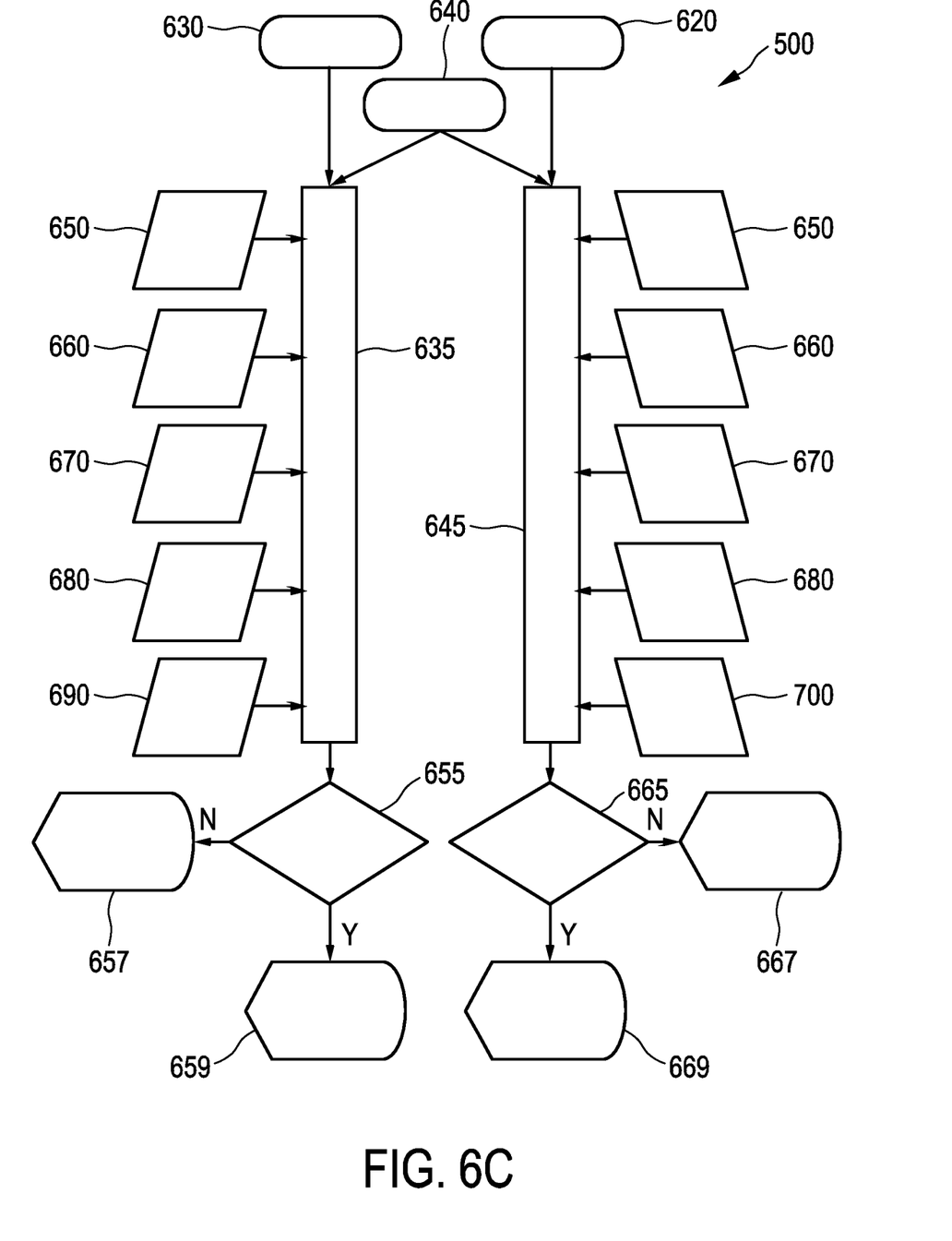

FIGS. 6A-6C schematically and exemplarily illustrate a flowchart of an example of an assessing method 500 according to the invention. Assessing method 500 begins at start 505.

In a first step 515, it is decided whether activity is recognized based on a provided activity recognition 510. In case activity, such as cycling or running, is recognized, the method is started over again with step 505. In case no activity is recognized, the method proceeds to decision 525.

At step 525, it is decided whether a provided activity level 520, for instance a magnitude of a motion signal, is below a predefined threshold. In case the activity level 520 is not below with a predefined threshold, the method is started over again with step 505. In the contrary, in case the activity level 520 is below the predefined threshold, the method proceeds to decision 535.

At step 535, it is decided whether the subject is recovering from activity based on a provided activity history 530. In case the subject is recovering from activity, the method is started over again with step 505. In the contrary, in case the subject is not recovering from activity, the method proceeds to step 545.

At step 545, a provided heart rate 540, which is provided for instance from heart rate determination unit 40, is stored within a heart rate storage 546. The method proceeds with step 555.

At step 555, it is decided whether data stored in heart rate storage 546 is sufficient to build a histogram. In case the data is not sufficient to build the histogram, the method is started over again with step 505. In case the data in heart rate storage 546 is sufficient to build the histogram, the method proceeds to step 565. In this example, data corresponding to 24 hours of monitoring time usually yield sufficient data during resting periods to build the histogram. However, the sufficiency criterion can be arbitrarily defined as desired.

In step 565, based on the data in heart rate storage 546, a heart rate histogram 560 is built and provided, for instance by heart rate histogram determination unit 60. The method then proceeds to step 585, which is illustrated on the second page of the flowchart in FIG. 6B and connected by an off page connector 575 on FIGS. 6A and 6B, respectively.

At step 585 it is decided whether the heart rate distribution represented by the provided heart rate histogram 560 is unimodal. In case the heart rate distribution is unimodal, a single unimodal distribution 592 is provided. In the contrary, in case the heart rate distribution is not unimodal, the histogram is separated into a number of unimodal distributions in step 595. As a result, exemplarily unimodal distributions 592, 594 and 596 are provided. However, it is obvious that also a different number of unimodal distributions different from the three indicated in the flowchart can be provided.

The method continues with step 605, in which it is decided whether a majority of values in any of the provided distributions is below a lower threshold.

In case no majority of values in any distribution is below the lower threshold, in step 615 it is decided whether a majority of values in any of the distributions is above an upper threshold. In general, in case a majority of values in any of the distributions is below or above the lower or upper threshold, respectively, an abnormality can be determined in the heart rate.

In case in step 615 it is determined that no majority of the values in any distribution are above the upper threshold, the heart rate is normal and the procedure ends in step 610. The procedure can then start over and return to start 505.

In case in step 615 it is determined that the majority of values in any of the distributions is above the upper threshold, tachycardia 620 is determined as an abnormality. The determined condition has to be further assessed, which will be described with reference to FIG. 6C below.

In case in step 605 it is determined that a majority of values in any distribution is below the lower threshold, it is proceeded with step 625, in which it is decided whether the majority of values in any of the distributions is above an upper threshold. In the negative, only bradycardia 630 is determined. However, in the affirmative, bradycardia and tachycardia are detected and the method ends with condition 640.

FIG. 6C illustrates a further subset of method 500 following the determination of tachycardia 620, bradycardia 630 or bradycardia and tachycardia 640.

In case of either bradycardia 630 or bradycardia and tachycardia 640, in step 635 the origin of the determined bradycardia is assessed. For instance, it is determined whether bradycardia is of pathological origin or not. In step 635, a user profile 650, symptoms of the subject 660, medication of the subject 670, a sleep profile of the subject 680 and a fitness level of the subject 690 are provided to assess whether bradycardia is pathological or not. For example, young individuals such as children and adolescents tend to have higher resting heart rate than adults and females tend to have higher resting heart rates than males. Further, the user profile can also indicate a relative risk of the subject to experience a pathological heart condition. Symptoms indicating pathological bradycardia can include fatigue, dizziness, light headedness, fainting or near-fainting spells. In extreme cases, cardiac arrest can occur with insufficient blood flow caused by pathological bradycardia. Sinus, i.e. non-pathological, bradycardia can be caused by medication such as digoxine, beta blockers or amiodarone, or also certain eye drops (timolol). Non-pathological bradycardia is more likely and more usual to occur during sleep and common in healthy, athletic individuals.

In step 655 it is decided whether bradycardia has been determined to be of pathological origin and in case of a non-pathological origin, the subject is informed in step 657 to have had non-pathological bradycardia, and in the contrary, in step 659 to have had pathological bradycardia. The information in steps 657 and 659 can be directly fed back to the subject or stored and otherwise used for later processing.

In step 645, in case tachycardia 620 or bradycardia and tachycardia 640 have been determined as the abnormality, the origin of the tachycardia is assessed. For instance, it can be determined whether tachycardia is of pathological origin or not. Also in this respect, user profile 650, symptoms 660, medication 670 and the sleep profile 680 are employed. Further, a stress level 700 of the subject can be employed as an additional parameter. Concerning the user profile, sinus rhythm has a maximum rate which decreases with age, such that heart rates above a certain upper threshold would be unexpected even during intensive exercise, depending on age. Pathological tachycardia can cause symptoms such as dizziness, light headedness, rapid heartbeat or palpitations, angina (chest pain), shortness of breath, unconsciousness, or cardiac arrest. Sinus tachycardia may be present during conditions such as fever, pain or dehydration. Bronchodilators or dopamine could lead to sinus tachycardia, as well as omitting beta blocker medication. Also the use of caffeine and alcohol can induce sinus tachycardia. Non-pathological tachycardia is less likely to occur during sleep and can occur as a consequence of mental stress.

Similar to step 655, in step 665 it is decided based on the assessment of step 645, whether tachycardia is of pathological origin. In the affirmative, in step 669, the subject is informed to have had pathological tachycardia. In the negative, in case tachycardia is determined not to be of pathological origin, the subject is informed in step 667 to have had non-pathological tachycardia.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. For example, although a PPG sensing unit in contact with the skin has been mainly disclosed in the description as being the PPG signal providing unit, the same invention holds for other optical signal providing units, like a laser speckle sensing unit, or PPG signal providing units not in contact with the skin, like a vital signs camera. Next to that, more than one PPG signal providing unit may be used.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the determination of a heart rate of the subject based on the PPG signal, the determination of a resting period during which the subject is at rest based on the motion signal, the determination of an abnormality of the heart rate based on the resting period and the assessment of the determined abnormality based on the subject specific parameter et cetera performed by one or several units or devices can be performed by any other number of units or devices. These procedures and/or the control of the assessing system for assessing a heart rate of a subject in accordance with the assessing method for assessing a heart rate of a subject can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The present invention relates to an assessing system, an assessing method and a computer program for assessing a heart rate of a subject. It finds application in categorizing a physiological response as a condition, in particular in the diagnosis of pathological tachycardia and bradycardia. The assessing system comprises a photoplethysmography PPG signal providing unit; a motion signal providing unit; a parameter providing unit for providing a subject specific parameter; a heart rate determination unit; a resting period determination unit; an abnormality determination unit for determining an abnormality of the heart rate based on the resting period; and an assessing unit for assessing the determined abnormality based on the subject specific parameter. The invention provides a system and a method, which allow for a more reliable assessment of a heart rate of a subject based on a PPG signal of the subject.

The invention claimed is:

1. An assessing system for assessing a heart rate of a subject, the assessing system comprising:

a photoplethysmography signal providing unit for providing a photoplethysmography signal indicative of a heartbeat of the subject;
a motion signal providing unit for providing a motion signal indicative of a motion of the subject;
a parameter providing unit for providing a subject specific parameter of the subject;
a heart rate determination unit for determining a heart rate of the subject based on the photoplethysmography signal;
a resting period determination unit for determining a resting period during which the subject is at rest based on the motion signal;
an abnormality determination unit for determining an abnormality of the heart rate during the resting period, wherein the abnormality determination unit is arranged to determine bradycardia and/or tachycardia based on an upper and lower threshold of the heart rate, respectively, as the abnormality of the heart rate;
an assessing unit for assessing if the determined abnormality is of a pathological origin based on the subject specific parameter;
a heart rate histogram determination unit for determining a histogram of values of the heart rate during the resting period; and
a heart rate distribution determination unit for determining a distribution of the values of the heart rate based on the histogram of values of the heart rate,
wherein the heart rate distribution determination unit is configured for determining a number of modes in the histogram and for determining a number of distributions based on the determined number of modes,
wherein the abnormality determination unit is configured for determining the abnormality of the heart rate based on the distribution, and
wherein the parameter providing unit is arranged to provide at least one of a profile, symptoms, a medication, a sleep profile, a fitness level and a stress level as the subject specific parameter.

2. The assessing system of claim 1, wherein the motion signal providing unit is configured to provide an accelerometer signal of the subject.

3. The assessing system of claim 1, wherein the resting period determination unit is arranged for determining an activity of the subject based on the motion signal and for determining the resting period as a period for which no activity can be determined based on the motion signal.

4. The assessing system of claim 3, wherein the resting period determination unit is arranged for excluding a transition period following an activity from the resting period.

5. The assessing system of claim 1, wherein the resting period determination unit is arranged for determining the resting period as a period for which a magnitude of the motion signal lies below a predefined threshold.

6. The assessing system of claim 5, wherein the assessing unit is configured to, in case the abnormality determination unit determines bradycardia as the abnormality, assess the determined abnormality based on the profile, the symptoms, the medication, the sleep profile and the fitness level of the subject.

7. The assessing system of claim 6, wherein the assessing unit is configured to, in case the abnormality determination unit determines tachycardia as the abnormality, assess the determined abnormality based on the profile, the symptoms, the medication, the sleep profile and the stress level of the subject.

8. The assessing system of claim 1, further comprising a feedback providing unit for providing feedback to the subject.

9. The assessing system according to claim 1, wherein the assessing system is implemented as a wrist based device.

10. A non-transitory computer-readable medium that stores therein a computer program product, which, when executed on a processor causes the processor to perform the following steps:
receiving a photoplethysmography signal indicative of a heartbeat of the subject;
receiving a motion signal indicative of a motion of the subject;
receiving a subject specific parameter of the subject;
determining a heart rate of the subject based on the photoplethysmography signal;
determining a resting period during which the subject is at rest based on the motion signal;
determining an abnormality of the heart rate during the resting period, wherein bradycardia and/or tachycardia are determined based on an upper and lower threshold of the heart rate, respectively, as the abnormality of the heart rate;
assessing if the determined abnormality is of a pathological origin based on the subject specific parameter;
determining a histogram of values of the heart rate during the resting period;
determining a distribution of the values of the heart rate based on the histogram of values of the heart rate;
determining a number of modes in the histogram;
determining a number of distributions based on the determined number of modes; and
determining the abnormality of the heart rate based on the distribution;
wherein at least one of a profile, symptoms, a medication, a sleep profile, a fitness level and a stress level is provided as the subject specific parameter.

11. The non-transitory computer-readable medium of claim 10, wherein the steps further comprise receiving an accelerometer signal of the subject.

12. The non-transitory computer-readable medium of claim 10, wherein the steps further comprise determining an activity of the subject based on the motion signal and determining the resting period as a period for which no activity can be determined based on the motion signal.

13. The non-transitory computer-readable medium of claim 10, wherein the steps further comprise excluding a transition period following an activity from the resting period.

14. The non-transitory computer-readable medium of claim 10, wherein the steps further comprise determining the resting period as a period for which a magnitude of the motion signal lies below a predefined threshold.

15. The non-transitory computer-readable medium of claim 10, wherein the steps further comprise assessing the determined abnormality based on the profile, the symptoms, the medication, the sleep profile and the fitness level of the subject when case the abnormality determination unit determines bradycardia as the abnormality.

16. The non-transitory computer-readable medium of claim 10, wherein the steps further comprise assessing the determined abnormality based on the profile, the symptoms, the medication, the sleep profile and the stress level of the subject when the abnormality determination unit determines tachycardia as the abnormality.

17. The non-transitory computer-readable medium of claim 10, wherein the steps further comprise generating feedback to be provided to the subject.

\* \* \* \* \*